United States Patent
Yoshino et al.

(10) Patent No.: US 9,775,501 B2
(45) Date of Patent: Oct. 3, 2017

(54) ENDOSCOPE AND ENDOSCOPE APPARATUS HAVING PIEZOELECTRIC ELEMENT WHICH SWINGS A FREE END OF AN OPTICAL ELEMENT THROUGH A JOINING MEMBER

(71) Applicant: OLYMPUS CORPORATION, Tokyo (JP)

(72) Inventors: Masahiro Yoshino, Sagamihara (JP); Tomoki Funakubo, Tama (JP); Atsuyoshi Shimamoto, Tokyo (JP); Yasunobu Iga, Tachikawa (JP); Mitsuru Namiki, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 331 days.

(21) Appl. No.: 14/203,763

(22) Filed: Mar. 11, 2014

(65) Prior Publication Data
US 2014/0194692 A1    Jul. 10, 2014

Related U.S. Application Data

(63) Continuation-in-part of application No. PCT/JP2012/074356, filed on Sep. 24, 2012.

(30) Foreign Application Priority Data

Nov. 9, 2011   (JP) ................................ 2011-245690

(51) Int. Cl.
*A61B 1/07*   (2006.01)
*A61B 1/00*   (2006.01)
(Continued)

(52) U.S. Cl.
CPC ............ *A61B 1/07* (2013.01); *A61B 1/00096* (2013.01); *A61B 1/00172* (2013.01);
(Continued)

(58) Field of Classification Search
CPC .. A61B 1/00172; A61B 5/0066; A61B 5/0068; A61B 5/0062; H01L 41/09; H01L 41/0475; H01L 41/0913; H01L 41/0966
See application file for complete search history.

(56) References Cited

U.S. PATENT DOCUMENTS 4,696,703 A * 9/1987 Henderson ............ C22C 45/006
148/403
5,135,295 A * 8/1992 Jen ........................ G02F 1/0134
385/128
(Continued)

FOREIGN PATENT DOCUMENTS

EP   1 077 360 A1   2/2001
EP   1 142 529 A1   10/2001
(Continued)

OTHER PUBLICATIONS

English Abstract of WO 2008/143623 A1, dated Nov. 27, 2008.
(Continued)

*Primary Examiner* — John P Leubecker
(74) *Attorney, Agent, or Firm* — Scully, Scott, Murphy & Presser, P.C.

(57) ABSTRACT

An endoscope has an insertion portion inserted through a living body, an illumination fiber arranged at a distal end of the insertion portion and irradiates the living body with illumination light, a detection fiber which detects return light from the living body, an actuator which swings a free end of the illumination fiber, and a ferrule which has a through-hole based on a diameter of the illumination fiber and is arranged between the illumination fiber and the actuator. The actuator has an actuator arranged at a first side face of the ferrule and an actuator arranged at a second side face of the ferrule that is different from a face point-symmetric to the first side face with respect to an axial direction of the illumination fiber.

17 Claims, 8 Drawing Sheets

(51) Int. Cl.
*G02B 23/24* (2006.01)
*G02B 26/10* (2006.01)

(52) U.S. Cl.
CPC ...... *A61B 1/00183* (2013.01); *G02B 23/2469* (2013.01); *G02B 26/103* (2013.01)

(56) References Cited

U.S. PATENT DOCUMENTS

| | | | |
|---|---|---|---|
| 6,023,406 A * | 2/2000 | Kinoshita | H01G 5/12 333/139 |
| 6,361,155 B1 * | 3/2002 | Kanda | B41J 2/14274 347/65 |
| 6,608,684 B1 * | 8/2003 | Gelikonov | A61B 1/00096 356/479 |
| 7,129,472 B1 * | 10/2006 | Okawa | A61B 1/00059 250/216 |
| 8,411,922 B2 | 4/2013 | Lee et al. | |
| 2001/0009345 A1 * | 7/2001 | Chang | C01G 25/006 310/358 |
| 2001/0018553 A1 | 8/2001 | Krattiger et al. | |
| 2002/0139920 A1 * | 10/2002 | Seibel | A61B 1/0008 250/208.1 |
| 2003/0206321 A1 | 11/2003 | Gelikonov et al. | |
| 2004/0122328 A1 * | 6/2004 | Wang | A61B 1/00048 600/476 |
| 2004/0254474 A1 * | 12/2004 | Seibel | A61B 5/0062 600/473 |
| 2005/0052753 A1 * | 3/2005 | Kanai | A61B 1/0008 359/642 |
| 2007/0055103 A1 | 3/2007 | Hoefig et al. | |
| 2007/0280614 A1 * | 12/2007 | Karasawa | A61B 1/00096 385/123 |
| 2008/0021282 A1 | 1/2008 | Hoeg et al. | |
| 2008/0081950 A1 * | 4/2008 | Koenig | A61B 1/00172 600/160 |
| 2008/0144998 A1 * | 6/2008 | Melville | G02B 26/103 385/51 |
| 2008/0249369 A1 * | 10/2008 | Seibel | A61B 1/0008 600/182 |
| 2008/0291597 A1 | 11/2008 | Seibel et al. | |
| 2009/0026888 A1 | 1/2009 | Melville | |
| 2009/0103882 A1 * | 4/2009 | Melville | A61B 1/0008 385/137 |
| 2009/0141997 A1 * | 6/2009 | Lee | A61B 1/0008 382/260 |
| 2009/0177042 A1 * | 7/2009 | Johnston | A61B 1/00172 600/178 |
| 2009/0244545 A1 | 10/2009 | Toida | |
| 2009/0251704 A1 | 10/2009 | Masuda | |
| 2010/0157039 A1 * | 6/2010 | Sugai | A61B 1/00009 348/68 |
| 2010/0168515 A1 * | 7/2010 | Sugimoto | A61B 1/0008 600/109 |
| 2010/0177368 A1 * | 7/2010 | Kobayashi | A61B 1/0008 359/198.1 |
| 2010/0179386 A1 * | 7/2010 | Kobayashi | A61B 1/0008 600/178 |
| 2010/0317923 A1 * | 12/2010 | Endo | A61B 1/0008 600/178 |
| 2011/0054252 A1 * | 3/2011 | Ozaki | A61B 1/00089 600/109 |
| 2013/0038173 A1 * | 2/2013 | Rogers | H01L 41/0913 310/326 |
| 2013/0257222 A1 * | 10/2013 | Funakubo | H01L 41/047 310/317 |
| 2013/0345508 A1 * | 12/2013 | Akui | A61B 1/00172 600/109 |
| 2015/0029570 A1 * | 1/2015 | Ito | G02B 23/26 359/198.1 |

FOREIGN PATENT DOCUMENTS

| | | |
|---|---|---|
| EP | 2 042 856 A2 | 4/2009 |
| JP | 2001-149304 A | 6/2001 |
| JP | 2001-174744 A | 6/2001 |
| JP | 2002-505890 A | 2/2002 |
| JP | 2004-024888 A | 1/2004 |
| JP | 2009-098112 A | 5/2009 |
| JP | 2009-212519 A | 9/2009 |
| JP | 2009-236614 A | 10/2009 |
| JP | 2010-075391 A | 4/2010 |
| JP | 2010-513949 A | 4/2010 |
| JP | 2010-148769 A | 7/2010 |
| JP | 2010-162089 A | 7/2010 |
| JP | 2010-527688 A | 8/2010 |
| JP | 2010-534862 A | 11/2010 |
| JP | 2011-004929 A | 1/2011 |
| JP | 2011-505190 A | 2/2011 |

OTHER PUBLICATIONS

English Abstract of WO 2009/014525 A1, dated Jan. 29, 2009.
English Abstract of WO 2008/076149 A1, dated Jun. 26, 2008.
Extended Supplementary European Search Report dated Apr. 29, 2015 from related European Application No. 12 84 8328.6.

* cited by examiner

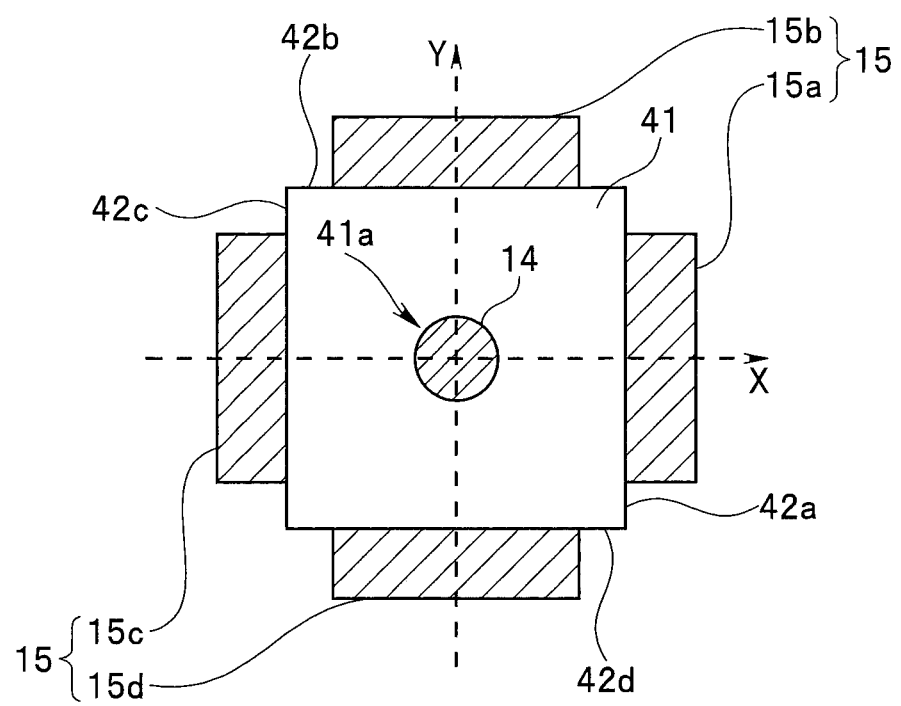

X-AXIS

Y-AXIS

ENDOSCOPE AND ENDOSCOPE APPARATUS HAVING PIEZOELECTRIC ELEMENT WHICH SWINGS A FREE END OF AN OPTICAL ELEMENT THROUGH A JOINING MEMBER

CROSS REFERENCE TO RELATED APPLICATION

This application is a continuation-in-part application of PCT/JP2012/074356 filed on Sep. 24, 2012 and claims benefit of Japanese Application No. 2011-245690 filed in Japan on Nov. 9, 2011, the entire contents of which are incorporated herein by this reference.

BACKGROUND OF THE INVENTION

1. Field of the Invention

The present invention relates to an endoscope and an endoscope apparatus and, more particularly, to an endoscope and an endoscope apparatus capable of stably driving an illumination fiber.

2. Description of the Related Art

A conventional scanning endoscope apparatus causes a distal end of an illumination fiber which guides light from a light source to perform scanning, receives return light from a subject with an optical fiber bundle which is arranged around the illumination fiber, converts chronologically detected light intensity signals into images.

For example, Japanese Patent Application Laid-Open Publication No. 2009-212519 discloses a scanning endoscope apparatus in which an illumination fiber is threaded through a piezoelectric element having a cylindrical shape, and the illumination fiber is resonated by two-dimensionally distorting the piezoelectric element to perform scanning with light.

Japanese Patent Application Laid-Open Publication No. 2010-513949 discloses a scanning endoscope apparatus in which a space between a piezoelectric element and a fiber for illumination is filled with an adhesive material, such as a bead, to fix together and integrate the piezoelectric element and the fiber for illumination.

Japanese Patent Application Laid-Open Publication No. 2011-4929 proposes an endoscope apparatus which senses temperature of a distal end portion of an insertion portion and performs feedback scanning and algorithm correction.

SUMMARY OF THE INVENTION

An endoscope according to one aspect of the present invention includes an insertion portion which is inserted through a living body, an optical element which is arranged at a distal end of the insertion portion and irradiates the living body with illumination light, a light-receiving portion which detects return light from the living body, a drive section which swings a free end of the optical element, and a joining member which has a through-hole based on a diameter of the optical element and is arranged between the optical element and the drive section, wherein the drive section has a first drive section which is arranged at a first side face of the joining member and a second drive section which is arranged at a second side face of the joining member that is different from a face point-symmetric to the first side face with respect to an axial direction of the optical element.

An endoscope apparatus according to one aspect of the present invention includes an endoscope having an insertion portion which is inserted through a living body, an optical element which is arranged at a distal end of the insertion portion and irradiates the living body with illumination light, a light-receiving portion which detects return light from the living body, a drive section which swings a free end of the optical element, and a joining member which has a through-hole based on a diameter of the optical element and is arranged between the optical element and the drive section, and a body apparatus having a control section which produces a drive signal to be outputted to the drive section of the endoscope. The drive section has a first drive section which is arranged at a first side face of the joining member and a second drive section which is arranged at a second side face of the joining member that is different from a face point-symmetric to the first side face with respect to an axial direction of the optical element, and the control section produces a first drive signal to be outputted to the first drive section and a second drive signal to be outputted to the second drive section and controls a phase difference between a phase of the first drive signal and a phase of the second drive signal on the basis of the number of axes of vibration.

BRIEF DESCRIPTION OF THE DRAWINGS

FIG. 2 is a cross-sectional view of an actuator according to the first embodiment;

DETAILED DESCRIPTION OF THE PREFERRED EMBODIMENTS

Embodiments of the present invention will be described below with reference to the drawings.

First Embodiment

A first embodiment will be described below.

A configuration of an endoscope apparatus having an endoscope according to the first embodiment will be described first with reference to FIGS. 1 and 2.

Figure 1:
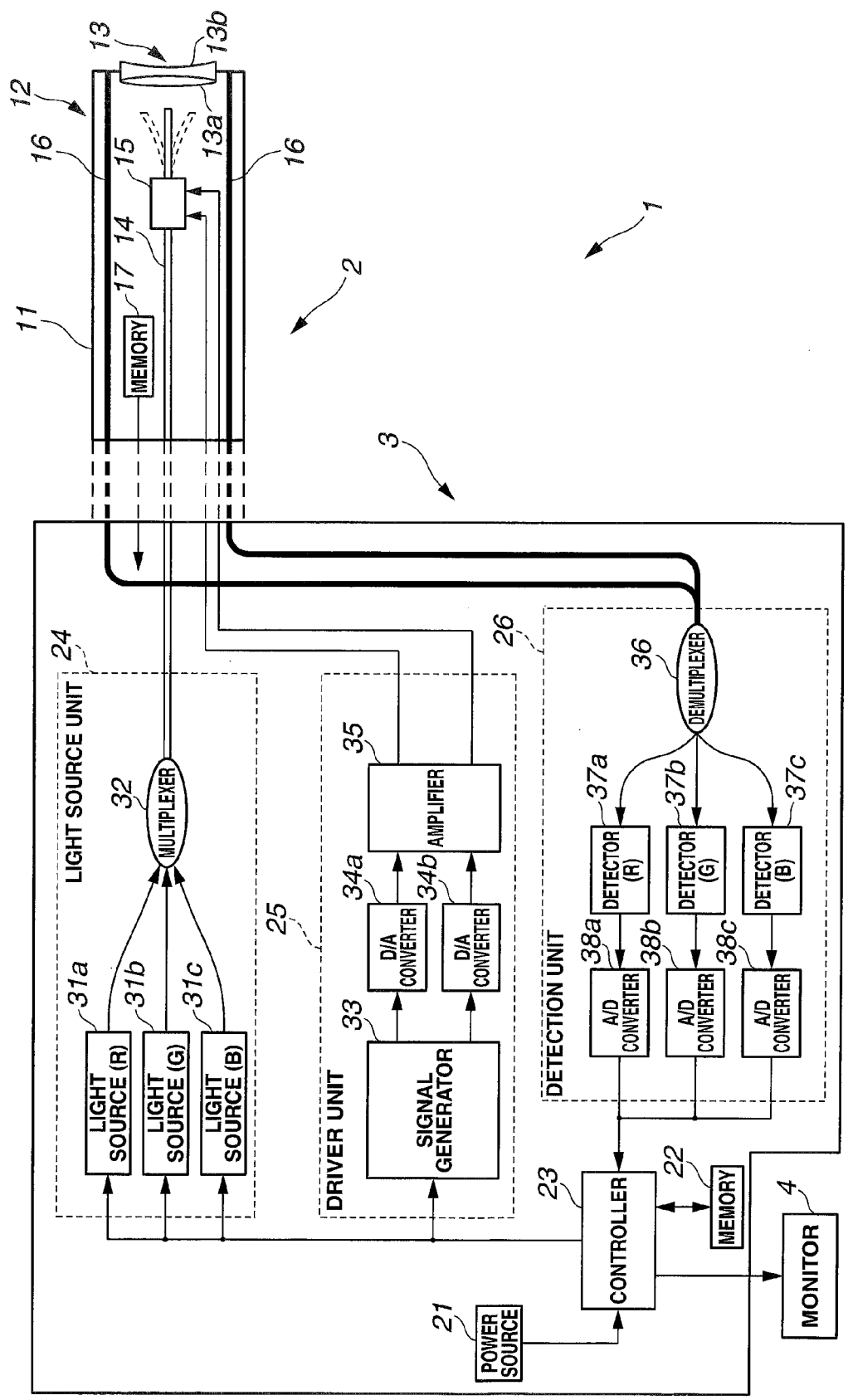
FIG. 1 is a view showing a configuration of an endoscope apparatus having an endoscope according to a first embodiment.

FIG. 1 is a view showing the configuration of the endoscope apparatus having the endoscope according to the first embodiment. FIG. 2 is a cross-sectional view of an actuator according to the first embodiment.

As shown in FIG. 1, an endoscope apparatus 1 is configured to have a scanning endoscope 2 which irradiates a subject with illumination light during scanning and obtains return light from the subject, a body apparatus 3 which is connected to the endoscope 2, and a monitor 4 which displays a subject image obtained by the body apparatus 3.

The endoscope 2 is mainly composed of a tubular body having predetermined flexibility and has an elongated insertion portion 11 which is to be inserted through a living body. A distal end portion 12 is provided on a distal end side of the insertion portion 11. A connector and the like (not shown) are provided on a proximal end side of the insertion portion 11. The endoscope 2 is configured to be detachable from the body apparatus 3 via the connector and the like.

A distal end optical system 13 which is composed of illumination lenses 13a and 13b is provided at a distal end face of the distal end portion 12. Inside the insertion portion 11, an illumination fiber 14 as an optical element which is inserted from the proximal end side toward the distal end side, guides light from a light source unit 24 (to be described later), and irradiates a living body with illumination light and an actuator 15 which is provided on a distal end side of the illumination fiber 14 and causes a distal end of the illumination fiber 14 to perform scanning in a desired direction on the basis of a drive signal from a driver unit 25 (to be described later) are provided. With the configuration, an object is irradiated with illumination light from the light source unit 24 which is guided by the illumination fiber 14.

Inside the insertion portion 11, a detection fiber 16 as a light-receiving portion which is inserted from the proximal end side toward the distal end side along an inner circumference of the insertion portion 11 and receives return light from a subject is also provided. A distal end face of the detection fiber 16 is arranged around the distal end optical system 13 at the distal end face of the distal end portion 12. The detection fiber 16 may be a bundle of at least two fibers. When the endoscope 2 is connected to the body apparatus 3, the detection fiber 16 is connected to a demultiplexer 36 (to be described later).

Inside the insertion portion 11, a memory 17 which stores various types of information on the endoscope 2 is further provided. When the endoscope 2 is connected to the body apparatus 3, the memory 17 is connected to a controller 23 (to be described later) via a signal line (not shown), and the various types of information on the endoscope 2 is read out by the controller 23.

The body apparatus 3 is configured to have a power source 21, a memory 22, the controller 23, the light source unit 24, the driver unit 25, and a detection unit 26.

The light source unit 24 is configured to have three light sources 31a, 31b, and 31c and a multiplexer 32.

The driver unit 25 is configured to have a signal generator 33, digital/analog (hereinafter referred to as D/A) converters 34a and 34b, and an amplifier 35.

The detection unit 26 is configured to have the demultiplexer 36, detectors 37a to 37c, and analog/digital (hereinafter referred to as A/D) converters 38a to 38c.

The power source 21 controls supply of power to the controller 23 in accordance with an operation of a power switch or the like (not shown). A control program and the like for control of the entire body apparatus 3 are stored in the memory 22.

When the controller 23 is supplied with power from the power source 21, the controller 23 reads out the control program from the memory 22, controls the light source unit 24 and the driver unit 25, and performs control that analyzes light intensity of return light from an object which is detected by the detection unit 26 and displays an obtained object image on the monitor 4.

The light sources 31a, 31b, and 31c of the light source unit 24 emit light components in different wavelength bands, such as light components in R (red), G (green), and B (blue) wavelength bands, to the multiplexer 32 under control of the controller 23.

The multiplexer 32 multiplexes the light components in the R, G, and B wavelength bands emitted from the light sources 31a, 31b, and 31c and emits multiplexed light to the illumination fiber 14.

The signal generator 33 of the driver unit 25 outputs a drive signal for causing the distal end of the illumination fiber 14 to perform scanning in the desired direction, e.g., in a spiral manner, under control of the controller 23. More specifically, the signal generator 33 outputs a drive signal which drives the distal end of the illumination fiber 14 in leftward and rightward directions (in an X-axis direction) with respect to an insertion axis of the insertion portion 11 to the D/A converter 34a and outputs a drive signal which drives the distal end in upward and downward directions (in a Y-axis direction) with respect to the insertion axis of the insertion portion 11 to the D/A converter 34b.

The D/A converters 34a and 34b convert the respective inputted drive signals from a digital signal into an analog signal and output the converted drive signals to the amplifier 35. The amplifier 35 amplifies the inputted drive signals and outputs the amplified drive signals to the actuator 15.

The actuator 15 as a drive section swings the distal end (a free end) of the illumination fiber 14 on the basis of the drive signals from the amplifier 35 to perform scanning in a spiral manner. With the configuration, a subject is sequentially irradiated with light emitted from the light source unit 24 to the illumination fiber 14 in a spiral manner.

The detection fiber 16 receives return light which is reflected by a surface region of the subject and guides the received return light to the demultiplexer 36.

The demultiplexer 36 is, for example, a dichroic mirror and demultiplexes the return light in predetermined wavelength bands. More specifically, the demultiplexer 36 demultiplexes the return light guided by the detection fiber 16 into return light components in the R, G, and B wavelength bands and outputs the return light components in the R, G, and B wavelength bands to the detectors 37a, 37b, and 37c, respectively.

The detectors 37a, 37b, and 37c detect light intensity of the return light components in the R, G, and B wavelength bands, respectively. Light intensity signals detected by the detectors 37a, 37b, and 37c are outputted to the A/D converters 38a, 38b, and 38c, respectively.

The A/D converters 38a to 38c convert the light intensity signals respectively outputted from the detectors 37a to 37c from an analog signal into a digital signal and output the converted light intensity signals to the controller 23.

The controller 23 subjects the digital signals from the A/D converters 38a to 38c to predetermined image processing to produce an object image and displays the object image on the monitor 4.

A detailed configuration of the actuator 15 provided inside the insertion portion 11 will be described with reference to FIG. 2.

As shown in FIG. 2, a ferrule 41 as a joining member is arranged between the illumination fiber 14 and the actuator 15. The ferrule 41 is a member used in a field of optical communication, and zirconia (ceramic), nickel, or the like is used as the material. Center hole drilling with high accuracy (e.g., ±1 μm) with respect to an outer diameter (e.g., 125 μm) of the illumination fiber 14 can be easily implemented.

As shown in FIG. 2, the ferrule 41 is a rectangular column and has side faces 42a and 42c which are perpendicular to the X-axis direction and side faces 42b and 42d which are perpendicular to the Y-axis direction. Note that the ferrule 41 is not limited to a rectangular column and may be a polygonal column. A through-hole 41a based on a diameter of the illumination fiber 14 is provided substantially at a center of the ferrule 41. The ferrule 41 is subjected to center hole drilling, and the illumination fiber 14 is fixed to the ferrule 41 with, e.g., an adhesive. More specifically, the ferrule 41 is provided such that the through-hole 41a is located at centers of a nearer end and a farther end face in the ferrule 41 and holds the illumination fiber 14 as an optical fiber. The center hole drilling is performed to minimize a clearance (space), and an adhesive layer is made as thin as possible. A low-viscosity adhesive is used as the adhesive.

The actuator 15 is composed of actuators 15a to 15d. The actuators 15a to 15d are located at the respective side faces 42a to 42d, respectively, of the ferrule 41 as the rectangular column. The actuators 15a to 15d are, for example, piezoelectric elements (piezo elements) and each expand or contract in accordance with a drive signal from the driver unit 25. In particular, the actuators 15a and 15c are driven in accordance with a drive signal from the D/A converter 34a while the actuators 15b and 15d are driven in accordance with a drive signal from the D/A converter 34b. With the configuration, the actuators 15a to 15d swing the distal end of the illumination fiber 14 and cause the distal end of the illumination fiber 14 to perform scanning in a spiral manner. Note that the actuators 15a to 15d are not limited to piezoelectric elements and may be, for example, coils which are electromagnetically driven.

Figure 9:
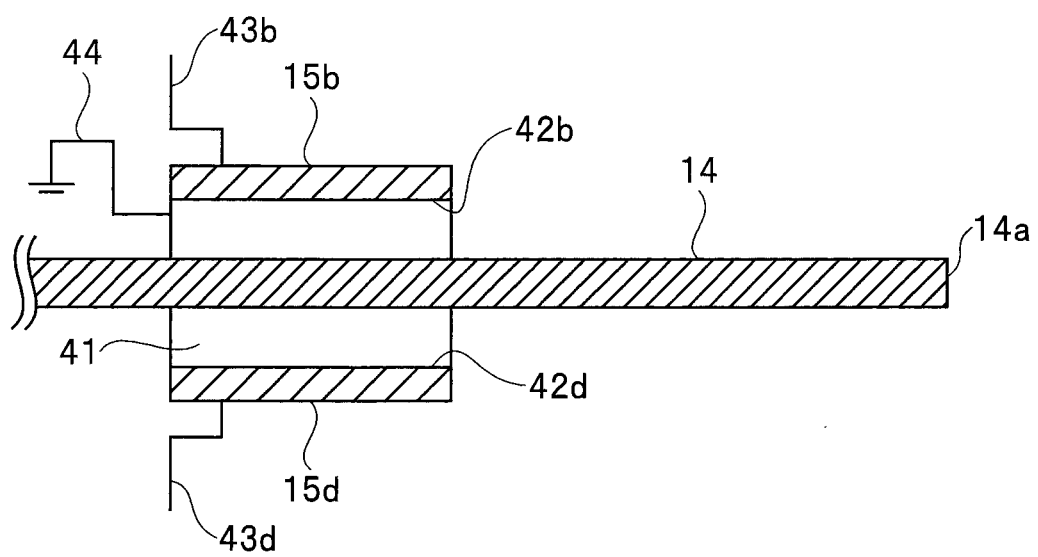
FIG. 9 is a cross-sectional view of the actuator according to the first embodiment along the Y-axis in FIG. 2.

FIG. 9 is a cross-sectional view of the actuator according to the first embodiment along the Y-axis in FIG. 2. The actuators 15a to 15d are formed in a flat plate shape. More specifically, as shown in FIG. 9, the plate-shaped actuators 15a to 15d are respectively attached to the side faces 42a to 42d of the rectangular column-shaped ferrule 41 with electrically-conductive adhesive or the like. With such a configuration, even the illumination fiber 14 having a circular cross section (see FIG. 2) and a thin diameter is used, the ferrule 41 is capable of stably holding the actuators 15a to 15d, and also capable of improving the transmission efficiency of the vibration. Note that FIG. 9 illustrates only the actuators 15b and 15d respectively attached to the side faces 42b and 42d. However, it is supposed that also the actuators 15a and 15c are respectively attached to the side faces 42a and 42c.

In addition, as shown in FIG. 9, drive signal lines 43a to 43d are respectively connected to outer faces of the actuators 15a to 15d, and the drive signal from the amplifier 35 of the driver unit 25 is supplied to the drive signal lines. Note that FIG. 9 illustrates only the drive signal lines 43b and 43d respectively connected to the outer faces of the actuator 15b and 15d. However, it is supposed that also the drive signal lines 43a and 43c are respectively connected to the outer faces of the actuators 15a and 15c.

The drive signal is supplied to the drive signal lines 43a and 43c, in order to cause the distal end of the illumination fiber 14 to swing along the X-axis in FIG. 2. In addition, the drive signal is supplied to the drive signal lines 43b and 43d, in order to cause the distal end of the illumination fiber 14 to swing along the Y-axis in FIG. 2.

If a conductive material, such as nickel, is used for the ferrule 41, the ferrule 41 itself is made to serve as a GND electrode for the actuators 15a to 15d. If a non-conductive material, such as zirconia, is used for the ferrule 41, a surface of the ferrule 41 is subjected to conductive film processing, and the surface is made to serve as the GND electrode for the actuators 15a to 15d. Furthermore, as shown in FIG. 9, the GND electrode connected to a GND signal line 44 is provided on a bottom face (more specifically, a surface which is farthermost from the distal end face 14a of the illumination fiber 14) of the ferrule 41 to ground (earth) the electrode, thereby also enabling simple and stable driving.

As described above, in the endoscope 2, the insertion of the ferrule 41 that is a joining member subjected to high-accuracy center hole drilling between the actuator 15 and the illumination fiber 14 makes the adhesive layer required to fix the illumination fiber 14 and the ferrule 41 as thin as possible, minimizes effects of a change in temperature, and implements stable driving of the illumination fiber 14.

Action of the endoscope apparatus 1 with the above-described configuration will be described.

Figure 3A:
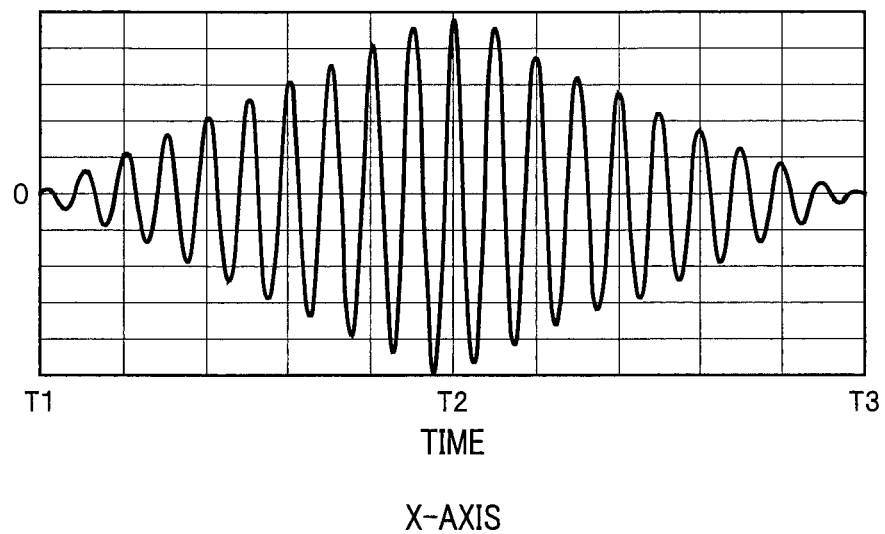
FIG. 3A is a chart for explaining an example of a signal waveform supplied to the actuator.
Figure 3B:
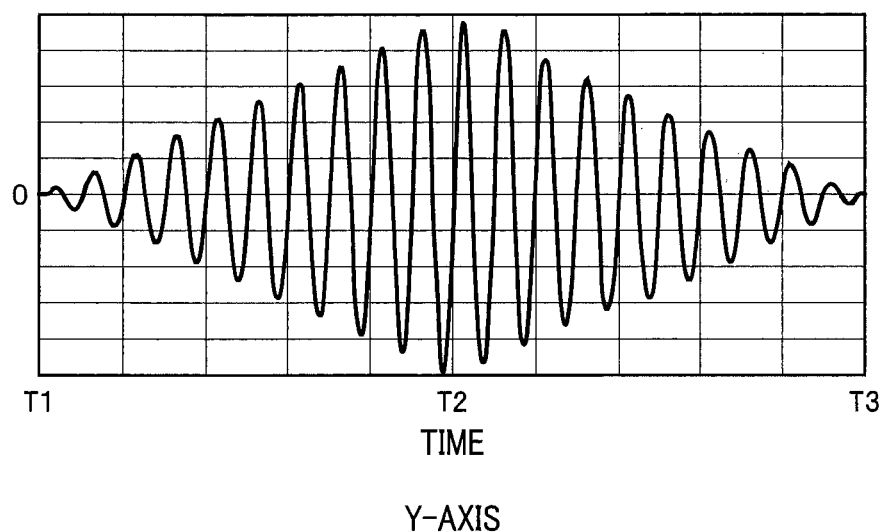
FIG. 3B is a chart for explaining an example of a signal waveform supplied to the actuator.
Figure 4:
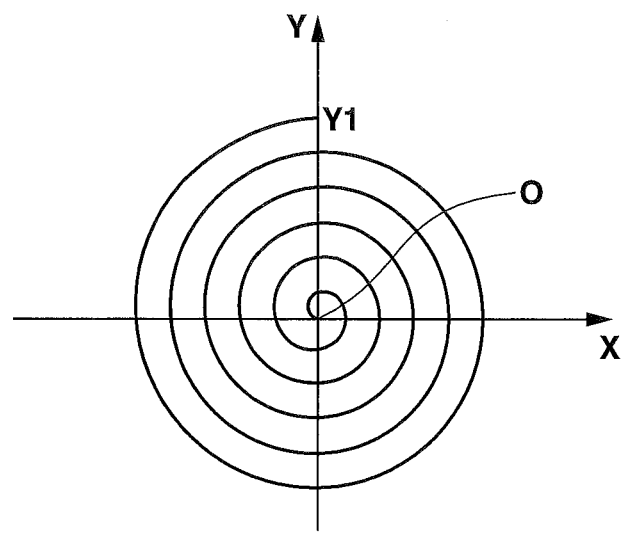
FIG. 4 is a view for explaining an example of a scan trajectory of an illumination fiber.

FIGS. 3A and 3B are charts for explaining examples of a signal waveform supplied to the actuator 15. FIG. 4 is a view for explaining an example of a scan trajectory of the illumination fiber 14.

FIG. 3A is a signal waveform of a drive signal which is outputted from the D/A converter 34a via the amplifier 35. The signal waveform belongs to a drive signal for driving the illumination fiber 14 in the X-axis direction and is supplied to the actuators 15a and 15c.

FIG. 3B is a signal waveform of a drive signal which is outputted from the D/A converter 34b via the amplifier 35. The signal waveform belongs to a drive signal for driving the illumination fiber 14 in the Y-axis direction and is supplied to the actuators 15b and 15d.

The signal waveform for the Y-axis direction is a signal waveform which is 90° out of phase with the signal waveform for the X-axis direction. More specifically, a phase difference between the signal waveform for the X-axis direction and the signal waveform for the Y-axis direction is calculated by (equation 1) below if the number N of axes of vibration is an even number and is calculated by (equation 2) below if the number N of axes of vibration is an odd number.

$$\text{phase difference} = 360°/(2 \times \text{the number } N \text{ of axes of vibration}) \quad \text{(equation 1)}$$

$$\text{phase difference} = 360°/\text{the number } N \text{ of axes of vibration} \quad \text{(equation 2)}$$

Since the number N of axes of vibration is 2 (an even number: an X-axis and a Y-axis) in the present embodiment, the phase difference is calculated to be 90° from (equation 1) above.

As described above, the driver unit 25 produces a first drive signal which is outputted to the actuators 15a and 15c and a second drive signal which is outputted to the actuators 15b and 15d and constitutes a control section which controls a phase difference between a phase of the first drive signal and a phase of the second drive signal on the basis of the number N of axes of vibration.

As shown in FIGS. 3A and 3B, the signal waveforms increase gradually in amplitude from time T1 to time T2 and have maximum amplitude values at time T2. The signal waveforms then decrease gradually from time T2 to time T3 and have minimum amplitude values at time T3.

A scan trajectory of the illumination fiber 14 in the case is a trajectory shown in FIG. 4. The distal end of the illumination fiber 14 is located at an intersection O of the X-axis and the Y-axis at time T1. When the signal waveforms increase in amplitude from time T1 to time T2, the distal end of the illumination fiber 14 performs scanning in a spiral manner outward from the intersection O. At time T2, the distal end is located, for example, at an intersection Y1 with the Y-axis. When the signal waveforms decrease in amplitude from time T2 to time T3, the distal end of the illumination fiber 14 performs scanning in a spiral manner inward from the intersection Y1, which is not shown. At time T3, the distal end is located at the intersection O.

As described above, the endoscope 2 is configured such that the ferrule 41 that is the joining member subjected to the high-accuracy center hole drilling is inserted between the actuator 15 and the illumination fiber 14. The configuration makes the adhesive layer required to fix the illumination fiber 14 and the ferrule 41 as thin as possible and minimizes effects of a change in temperature.

Thus, in an endoscope according to the present embodiment, an adhesive layer which fixes an illumination fiber has been thinned to reduce effects of a change in temperature. With the configuration, the endoscope can stably drive the illumination fiber.

(Modification)

Other configuration examples of the actuator will be described with reference to FIGS. 5 and 6.

Figure 5:
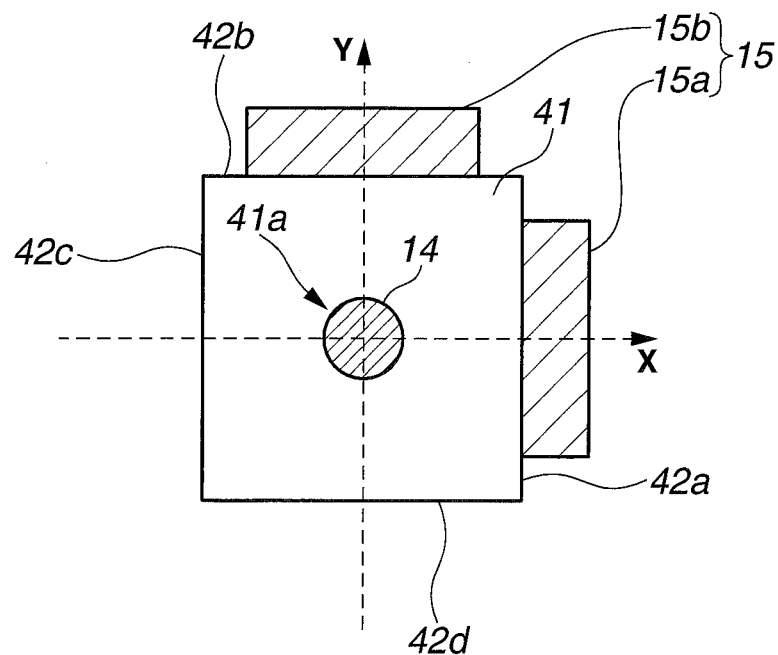
FIG. 5 is a view for explaining another configuration example of the actuator.
Figure 6:
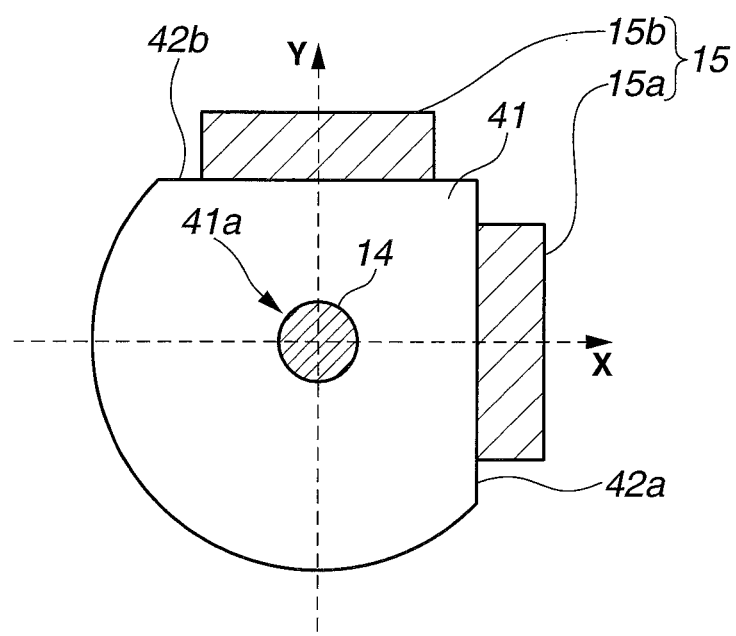
FIG. 6 is a view for explaining another configuration example of the actuator.

FIGS. 5 and 6 are views for explaining the other configuration examples of the actuator.

Although the actuators 15a to 15d are provided at the respective side faces 42a to 42d of the ferrule 41 in FIG. 2, the actuators 15a and 15b are provided at the side faces 42a and 42b of the ferrule 41 in FIG. 5. If the number M of side faces of the ferrule 41 is an odd number, M actuators need to be provided. On the other hand, if the number M of side faces of the ferrule 41 is an even number, at least M/2 (M is the number of side faces) actuators may be provided. Since the number M of side faces is 4 in the present embodiment, at least two actuators, the actuators 15a and 15b in the modification, may be provided.

The actuator 15a is arranged at the side face 42a as a first side face of the ferrule 41, and the actuator 15b is arranged at the side face 42b as a second side face of the ferrule 41 that is different from the side face 42c point-symmetric to the side face 42a with respect to an axial direction of the illumination fiber 14. More specifically, the two actuators 15a and 15b are arranged at either one of the side faces 42a and 42c perpendicular to the X-axis and at either one of the side faces 42b and 42d perpendicular to the Y-axis.

The above-described configuration allows implementation of the scan trajectory in FIG. 4 with the number of actuators smaller than the number of actuators in FIG. 2.

Shapes of the side faces 42c and 42d in FIG. 5 where the actuators 15a and 15b are not arranged are not limited to a polygonal column. For example, as shown in FIG. 6, the shapes may be a cylindrical shape.

Second Embodiment

A second embodiment will be described.

Figure 7:
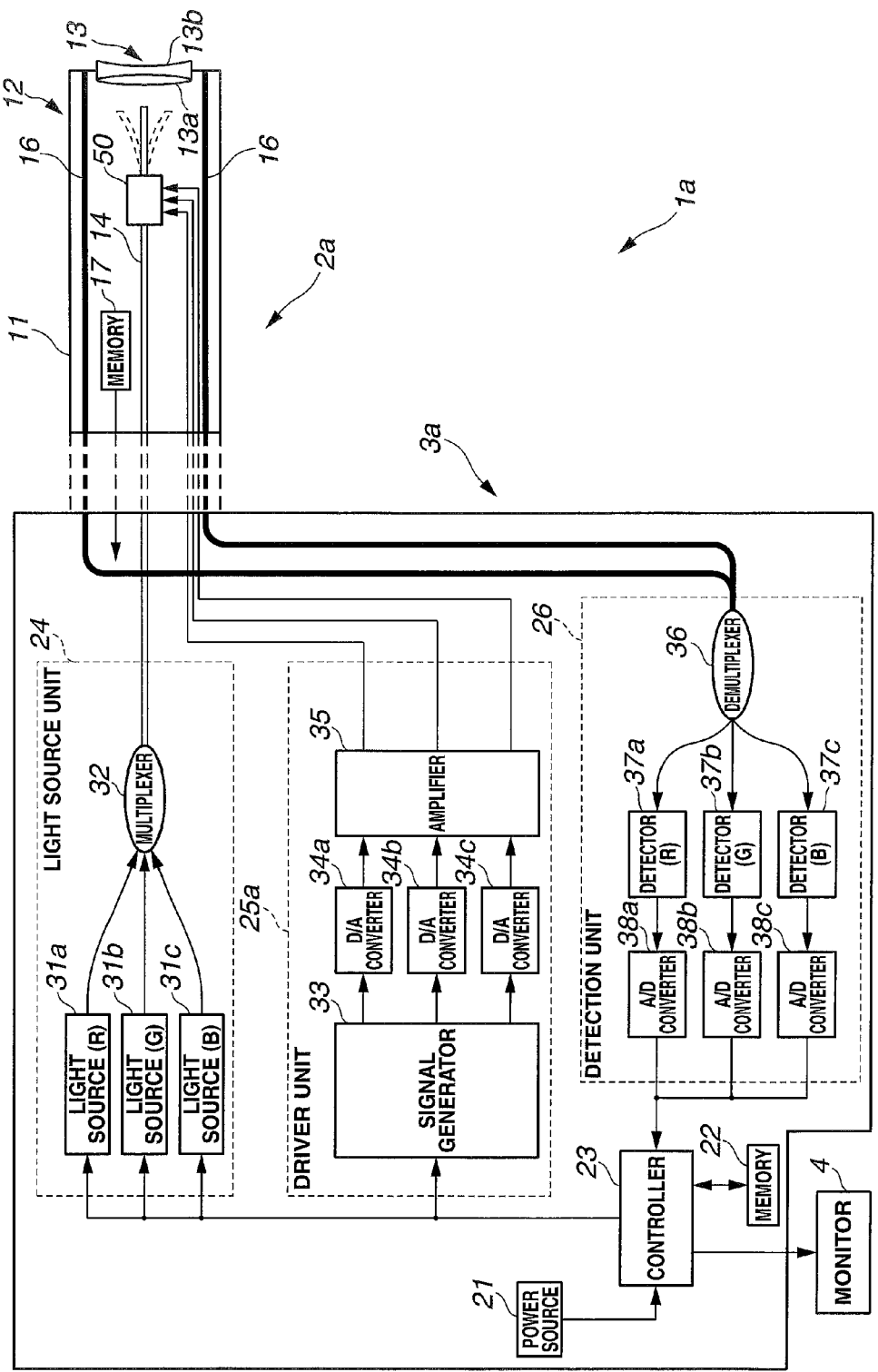
FIG. 7 is a view showing a configuration of an endoscope apparatus having an endoscope according to a second embodiment.
Figure 8:
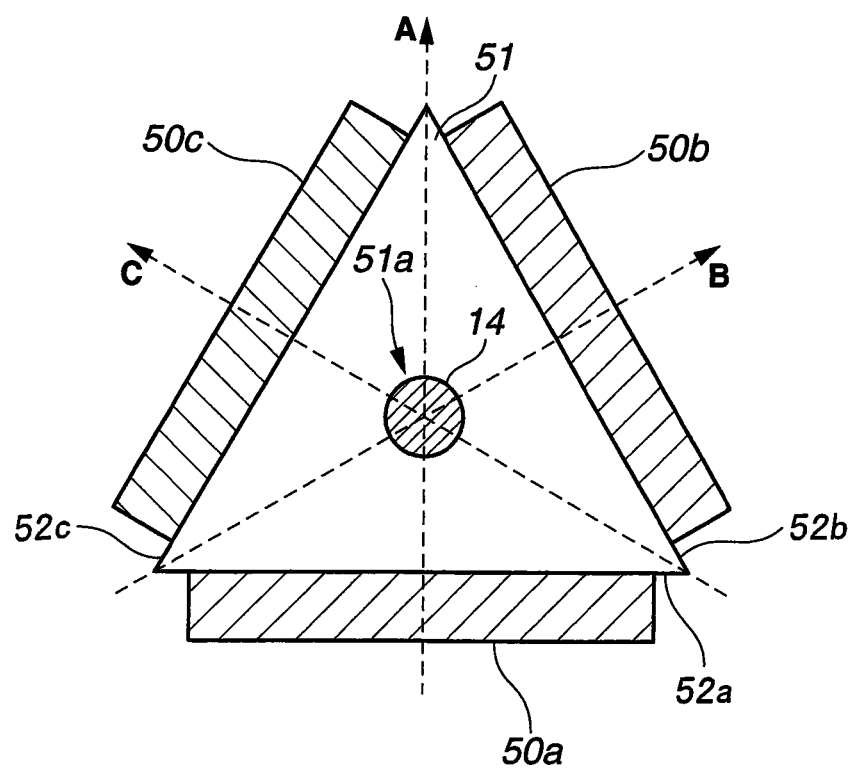
FIG. 8 is a cross-sectional view of an actuator according to the second embodiment.

FIG. 7 is a view showing a configuration of an endoscope apparatus having an endoscope according to the second embodiment. FIG. 8 is a cross-sectional view of an actuator according to the second embodiment. Note that components in an endoscope apparatus 1a of FIG. 7 which are identical to the components in the endoscope apparatus 1 according to the first embodiment are denoted by identical reference numerals and that a description of the components will be omitted.

The endoscope apparatus 1a according to the present embodiment is constructed using an endoscope 2a and a body apparatus 3a instead of the endoscope 2 and the body apparatus 3 in FIG. 1. The endoscope 2a is constructed using an actuator 50 instead of the actuator 15 in FIG. 1. The body apparatus 3a is constructed using a driver unit 25a instead of the driver unit 25 in FIG. 1.

As shown in FIG. 8, a ferrule 51 as a joining member is arranged between an illumination fiber 14 and the actuator 50. The ferrule 51 is a triangular column and has a side face 52a which is perpendicular to an A-axis, a side face 52b which is perpendicular to a B-axis, and a side face 52c which is perpendicular to a C-axis. A through-hole 51a based on a diameter of the illumination fiber 14 is provided substantially at a center of the ferrule 51, as in the first embodiment. The ferrule 51 is subjected to center hole drilling, and the illumination fiber 14 is fixed to the ferrule 51 with, e.g., an adhesive.

As shown in FIG. 8, the actuator 50 is composed of an actuator 50a which swings a distal end of the illumination fiber 14 in an A-axis direction, an actuator 50b which swings the distal end in a B-axis direction, and an actuator 50c which swings the distal end in a C-axis direction. The actuators 50a to 50c are arranged at the side faces 52a to 52c, respectively, of the ferrule 51.

The driver unit 25a is constructed by adding a D/A converter 34c to the driver unit 25 in FIG. 1. A signal generator 33 of the driver unit 25a outputs a drive signal which drives the distal end of the illumination fiber 14 in the A-axis direction in FIG. 8 to a D/A converter 34a, outputs a drive signal which drives the distal end in the B-axis direction to a D/A converter 34b, and outputs a drive signal which drives the distal end in the C-axis direction to the D/A converter 34c, under control of a controller 23.

The D/A converters 34a to 34c convert the respective inputted drive signals from a digital signal into an analog signal and output the converted drive signals to an amplifier 35. The amplifier 35 amplifies the inputted drive signals and outputs the amplified drive signals to the actuator 50. More specifically, the amplifier 35 supplies the drive signal inputted from the D/A converter 34a to the actuator 50a, supplies the drive signal inputted from the D/A converter 34b to the actuator 50b, and supplies the drive signal inputted from the D/A converter 34c to the actuator 50c. Since the number N of axes of vibration in the present embodiment is 3 (an odd number: the A-axis, the B-axis, and the C-axis), phase differences among signal waveforms of the drive signals supplied to the actuators 50a to 50c are calculated to be 120° respectively from (equation 2) above. That is, a signal waveform 120° out of phase with a signal waveform supplied to the actuator 50a is supplied to the actuator 50b, and a signal waveform 240° out of phase with the signal waveform supplied to the actuator 50a is supplied to the actuator 50c. With the supply of the drive signals to the actuators 50a to 50c, the distal end of the illumination fiber 14 is made to perform scanning in a spiral manner. A subject is sequentially irradiated with light emitted from a light source unit 24 to the illumination fiber 14 in a spiral manner.

The signal generator 33 of the driver unit 25 outputs a drive signal for causing the distal end of the illumination fiber 14 in a desired direction, e.g., in a spiral manner, under control of the controller 23. More specifically, the signal generator 33 outputs a drive signal which drives the distal end of the illumination fiber 14 in leftward and rightward directions (in an X-axis direction) with respect to an insertion axis of the insertion portion 11 to the D/A converter 34a and outputs a drive signal which drives the distal end in upward and downward directions (in a Y-axis direction) with respect to the insertion axis of the insertion portion 11 to the D/A converter 34b.

The D/A converters 34a and 34b convert the respective inputted drive signals from a digital signal into an analog signal and output the converted drive signals to the amplifier 35. The amplifier 35 amplifies the inputted drive signals and outputs the amplified drive signals to the actuator 50. The actuator 50 causes the distal end of the illumination fiber 14 to perform scanning in a spiral manner on the basis of the drive signals from the amplifier 35. With the configuration, a subject is sequentially irradiated with light emitted from the light source unit 24 to the illumination fiber 14 in a spiral manner.

As described above, in the endoscope 2a, the ferrule 51 as the triangular column is inserted between the actuator 50 and the illumination fiber 14. As in the first embodiment, the ferrule 51 can be subjected to high-accuracy center hole drilling. It is thus possible to make thinner an adhesive layer required to fix the illumination fiber 14 and the ferrule 51 and reduce effects of a change in temperature.

Therefore, in an endoscope according to the present embodiment, an adhesive layer which fixes an illumination fiber has been thinned to reduce effects of a change in temperature, as in the first embodiment. With the configuration, the endoscope can stably drive the illumination fiber.

The present invention is not limited to the above-described embodiments and modification, and various changes, alterations, and the like can be made without departing from scope of the present invention.

What is claimed is:

1. An endoscope comprising:
   an elongated insertion portion which is inserted in a subject;
   an optical element which is inserted from a proximal end side to a distal end side of the insertion portion and irradiates the subject with illumination light;
   a plurality of piezoelectric elements which swing a free end of the optical element; and
   a joining member which holds the free end of the optical element in a cantilever manner in a direction parallel to a longitudinal direction of the insertion portion, such that the free end of the optical element is unsupported in a radial direction,
   wherein the joining member includes a through-hole provided from a proximal end face to a distal end face of the joining member, the through-hole having a diameter substantially similar to the diameter of the optical element from the proximal end face to the distal end face, each of the plurality of piezoelectric elements being arranged on a side face of the joining member in a state where the optical element is inserted in the hole, and at least a surface of the joining member is formed by a conductive material and is a ground electrode for each of the plurality of piezoelectric elements.

2. The endoscope according to claim 1, wherein an entirety of the joining member is a conductive member.

3. The endoscope according to claim 2, wherein the joining member is made of nickel.

4. The endoscope according to claim 1, wherein the joining member is a non-conductive member, a surface of which is subjected to conductive film processing.

5. The endoscope according to claim 1, wherein the joining member is a ferrule.

6. The endoscope according to claim 1, wherein the side face includes first and second side faces, and the plurality of piezoelectric elements comprises first and second piezoelectric elements arranged on the first and second side faces, respectively.

7. The endoscope according to claim 6, wherein the ground electrode is a single ground electrode common to the first and second piezoelectric elements.

8. The endoscope according to claim 1, wherein an entirety of the joining member comprises a unitary piece of material.

9. The endoscope according to claim 1, wherein the plurality of piezoelectric elements are arranged asymmetrically around an outer periphery of a cross section the joining member, the cross section being perpendicular to the longitudinal direction of the optical element.

10. An endoscope comprising:
    an elongated insertion portion inserted in a subject;
    an optical element which is inserted from a proximal end side to a distal end side of the insertion portion and irradiates the subject with illumination light;
    a joining member having an elongated column shape and at least one planar side face, the joining member holding the optical element in a cantilever-manner in a direction parallel to a longitudinal direction of the insertion portion such that a free end of the optical element extends from a distal end face of the joining member; and
    a piezoelectric element which swings the free end of the optical element,
    wherein an entirety of the joining member comprises a unitary piece of material, the joining member having a through-hole with a diameter based on a diameter of the optical element, the through hole being provided from a proximal end face to the distal end face of the joining member,
    the optical element is inserted in the through-hole and is in contact with an inner circumferential surface of the through-hole; and
    the piezoelectric element having a side face wholly arranged only on the at least one planar side face of the joining member, the planar side face being parallel to a longitudinal direction of the fiber.

11. The endoscope according to claim 10, wherein the joining member has an elongated polygonal column-shape.

12. The endoscope according to claim 11, wherein the joining member includes three or more planar side faces.

13. The endoscope according to claim 10, wherein the through-hole is provided at centers of the proximal end face and the distal end face of the joining member.

14. The endoscope according to claim 10, wherein the optical element is fixed in the through-hole of the joining member with an adhesive.

15. The endoscope according to claim 10, wherein the joining member includes at least two planar surfaces orthogonal to each other, wherein the piezoelectric element is arranged on each of the two planar surfaces.

16. The endoscope according to claim 10, wherein the joining member is a ferrule.

17. The endoscope according to claim 10, wherein the piezoelectric element comprises a plurality of piezoelectric elements arranged asymmetrically around an outer periphery of a cross section of the joining element, the cross section being perpendicular to the longitudinal direction of the optical element.

* * * * *